United States Patent [19]

Sipos

[11] 4,314,991
[45] Feb. 9, 1982

[54] SULFONATED POLYAMINO ACIDS AS DENTAL PLAQUE BARRIERS

[75] Inventor: Tibor Sipos, Lebanon, N.J.

[73] Assignee: Johnson & Johnson Products Inc., New Brunswick, N.J.

[21] Appl. No.: 172,353

[22] Filed: Jul. 25, 1980

[51] Int. Cl.³ .................... A61K 7/16; C07C 103/52
[52] U.S. Cl. ............................... 424/56; 260/112.5 R
[58] Field of Search .................. 424/56; 260/112.5 R

[56] References Cited

U.S. PATENT DOCUMENTS 3,429,963  2/1969  Shedlovsky .......................... 424/56

Primary Examiner—Delbert R. Phillips
Attorney, Agent, or Firm—Irving Newman

[57] ABSTRACT

Polymers useful in compositions and methods for preventing the attachment of dental plaque to the surface of the teeth of mammals comprise certain sulfonated polyamino acids and salts thereof in a pharmaceutically acceptable vehicle and the periodic application thereof to teeth.

5 Claims, No Drawings

SULFONATED POLYAMINO ACIDS AS DENTAL PLAQUE BARRIERS

TECHNICAL FIELD

This invention relates to certain sulfonated polyamino acids, to oral hygiene compositions comprising these compounds, and to methods using such compositions to prevent attachment of bacteria to teeth. More particularly it relates to certain sulfonated polyamino acids, as well as selected pharmaceutically acceptable salts thereof, that have been found useful in inhibiting the agglutination of oral plaque on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, by fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

THE INVENTION

A number of hydrophilic sulfonic acid and sulfonic acid salt derivatives of certain aromatic polyamino acids have been synthesized and found to inhibit the deposition of dental plaque onto human teeth. These hydrophilic aromatic polyamino acid sulfonates have good film forming characteristics, and, accordingly, are applied to teeth from various dentrifrice formulations, mouth rinses, or other oral hygiene procedures. The sulfonated polymers of this invention are anionic in nature and substantially soluble in water or water/organic solvent vehicles, primarily because of the relatively high degree of sulfonation achieved during preparation of these derivatives. While the mechanism of action of the hydrophilic polymeric films in retarding plaque deposition is not known with absolute certainty, it is presumed that the films of anionically-charged polymers deposited on teeth effect a mutual repulsion between the negatively charged polymer film and the negatively charged microorganisms in oral fluids responsible for plaque generation. The sulfonated polyamino acid polymers of this invention are especially effective as components of dentrifrices and other oral hygiene preparations in reducing dental plaque deposition on teeth.

The preferred hydrophilic, aromatic, polyamino acid sulfonates useful for dental plaque control in accordance with the present invention include sulfonated homopolymers of phenylalanine and tyrosine. These polymers may be prepared by direct aromatic sulfonation of polyphenylalanine and polytyrosine. The sulfonic acid derivatives of these polyamino acids are rendered even more hydrophilic and water soluble by conversion to metal salts of certain of the group IA alkali metals, Group IIA, IIB, and IIIA multivalent metals, or to ammonium or amine salts.

Accordingly, the preferred hydrophilic, aromatic, polyamino acid sulfonates of this invention comprise a repeating unit selected from the group consisting of the repeating units having structure (A),

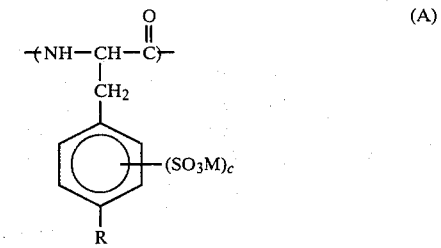

wherein R is selected from the group consisting of hydrogen and hydroxyl; subscript C, representing the average number of sulfonate groups per phenyl ring, has a value in the range of from about 0.5 to about 1.0; and M is an ion selected from the group consisting of lithium, sodium, potassium, calcium, magnesium, zinc, aluminum, hydrogen and the ammonium salts derived from ammonia and the pharmaceutically acceptable organic amines.

The polyphenylalanine and polytyrosine that may be sulfonated to prepare the plaque barrier agents of this invention are generally available from chemical supply houses. Alternatively, they can be synthesized by general organic reaction processes well known to those skilled in the art. Examples of available polyamino acids, which are sold by Sigma Chemical Company, St. Louis, Mo., that can be converted to the hydrophilic polymeric sulfonates of this invention include the following:

(a) Poly-L-Phenylalanine,
   (i) Type I-A (molecular weight 2,000–5,000);
   (ii) Type II (molecular weight 5,000–10,000);
(b) Poly-DL-Phenylalanine (molecular weight 10,000–30,000);
(c) Poly-D-Tyrosine,
   Type I-C (molecular weight 40,000–100,000);
(d) Poly-DL-Tyrosine,
(e) Poly-L-Tyrosine,
   Type I-B (molecular weight 40,000–100,000).

As will be appreciated regarding the foregoing precursors of the sulfonated polymers of the present invention, the polyphenylalanines have a structure containing repeating units of structure (A) wherein R is hydrogen but subscript c is zero (since unsulfonated), whereas the polytyrosines have the same general structure as the polyphenylalanines except that R is OH.

Suitable sulfonation agents for preparing the sulfonated polymeric plaque barriers of this invention include anhydrous sulfur trioxide, triethyl phosphate (TEP) complexes of sulfur trioxide, and chlorosulfonic acid. Due to the high reactivity of sulfur trioxide and its potent dehydration properties, sulfonation reactions with sulfur trioxide sometimes result in formation of highly insoluble polymer dispersions due to crosslinking caused by inter-polymer chain sulfone formation. In these situations, it is preferable to moderate the sulfonation reactivity by utilization of the sulfur trioxide complexes with triethyl phosphate (TEP), which minimize or essentially eliminate formation of crosslinked by-products.

Sulfonations are effected in solvents such as methylene chloride, 1,2-dichloroethane, and chloroform. Temperature control of the sulfonation reaction with sulfur trioxide and its complexes with TEP is not very critical. Acceptable results are obtained over a −20° C. to +40° C. range. Sulfonations are generally effected at ambient room temperatures, since the sulfonation exotherm is very mild.

The free sulfonic acid derivatives of the present invention are effective in reducing the deposition of plaque during in vitro testing, but these sulfonic acid polymers are too highly acidic to permit use in the oral environment unless suitably buffered. Certain salts of these polymeric sulfonic acids are preferred because of increased solubility in aqueous media and lower degree of acidity. These salts exhibit good plaque retardation barrier when tested in vitro.

The in vitro test procedure we have employed begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density on a 0 to 5 scale. Plaque barrier activity is reported as the % of average plaque reduction, as compared to appropriate controls, for ten subjects.

The degree of sulfonation (D.S.) of the sulfonated polyamino acids of this invention has a significant effect on the reduction of plaque deposition; a certain minimal D.S. is required for development of adequate plaque barrier activity. The D.S., defined herein as the average number of sulfonate or sulfonic acid groups per aromatic ring in the polymers of structure (A), can be varied by adjusting the conditions of the sulfonation reaction, such as the molar ratio of sulfonating agent to polymer. While the exact position of the sulfonic acid and sulfonic acid salt groups on the aromatic rings is often not known with certainty, this is not considered important in the practice of this invention.

The degree of sulfonation (D.S.) of the polyamino acids can be determined by any of several methods: (a) NMR analysis, (b) elemental analysis for sulfur to carbon ratio, or (c) direct titration of the sulfonic acid with standard sodium hydroxide. The NMR method is perhaps the more exact procedure, since it is not prone to interference by other impurities, such as with the acidimetric or elemental analyses.

The acidimetric procedure for D.S. determination involves titration of an accurately weighed two gram sample (±0.1 mg) of the sulfonic acid polymer, dissolved in about ten volumes of water, alcohol, or other solvents, with standardized sodium hydroxide to the potentiometric endpoint. The acidity, A, of the samples is expressed in milliequivalents/gram (meg/g). Using the acidity value, A, and the formula weight, R, of the unsulfonated repeat unit in the polymer, the D.S. is calculated from the following equations:

$$A = \frac{(ml. \text{ of titrant}) (Normality)}{\text{sample weight, in grams}}$$

$$D.S. = \frac{(R)(A)}{1000 - 80A}$$

The alkali metal salts of the sulfonated polymers are conveniently prepared by neutralization of a water or alcohol solution of the polymeric sulfonic acid derivative with alkali metal hydroxide solutions to the potentiometric endpoint. The salts are recovered by filtration, solvent stripping, or freeze drying, depending on the type of solvent used and whether the salt precipitates directly from the solvent media. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly, or they are isolated by solvent stripping. Purification of the sulfonate salt by dialysis is the preferred procedure for the more highly water soluble salts.

Multivalent metal salts of the sulfonated polymers, such as the calcium, magnesium, zinc, and aluminum salts, can be prepared by methods similar to those described above. In an alternate procedure, multivalent metal salts can be prepared by an ion-exchange reaction between the multivalent ion and either the free sulfonic acid or an alkali metal sulfonate derivative of the polymer. The neutralization and other salt forming reactions described above are essentially ion-exchange reactions. Ammonium salts of the sulfonic acid polymer can be prepared by direct addition of ammonia or a primary, secondary, or tertiary organic amine.

Poly(L-phenylalanine) sodium sulfonate of D.S. 0.8, for example, showed a plaque barrier activity of 63%. Generally, good plaque barrier activity is obtained when the average number of sulfonate groups per aromatic group in the polymers of this invention is at least about 0.5. Preferably, it is in the range of about 0.5 to about 1.0. By contrast, the non-sulfonated polymeric precursors are insoluble in water and exhibit no plaque barrier properties. Effective plaque barrier activity is seen only when the hydrophilic properties of the polymer are increased by introduction of either sulfonic acid or sulfonate salt functional groups.

While the molecular weight of the polymers of the present invention is not considered to be a critical factor, they generally have a weight average molecular weight within the broad range of from about 1,000 to about 200,000. A preferred molecular weight range is from about 2,000 to about 50,000.

EXAMPLE 1

Poly(L-phenylalanine) Sodium Sulfate

The sulfonation agent was prepared by the addition of 1.3 g (16.3 m moles) liquid sulfur trioxide to a solution of 1.0 g (5.4 m moles) triethyl phosphate in 16 ml. methylene chloride. This agent was then added dropwise over 7 minutes and at a temperature ranging from −1° C. to +7° C. to a stirred suspension of 0.8 g (5.4 m moles) poly(L-phenylalanine), having a molecular weight of about 2400, in 10 ml. methylene chloride. After stirring an additional 15 minutes, the yellow solids were filtered, washed with methylene chloride and ether, and dried to give 1.0 g of the polyphenylalanine sulfonic acid.

A solution of 0.8282 g of the polyphenylalanine sulfonic acid thus prepared, in 16 ml. methanol, was neutralized from an initial apparent pH of 0.2 to pH 8.0 with 5.8 ml. 0.556 N sodium hydroxide in methanol. Removal of the solvent from the neutralized solution gave 0.73 g of the polyphenylalanine sodium sulfonate. The D.S. was 0.8 based on the amount of alkali consumed in the neutralization step.

EXAMPLE 2

Poly(L-tyrosine) Sodium Sulfonate

In accordance with the procedure described in Example 1, poly(L-tyrosine) sodium sulfonate is prepared from poly(L-tyrosine) having a molecular weight of about 47,000 and a degree of polymerization of 280.

EXAMPLE 3

Poly(L-phenylalanine) Zinc Sulfonate

To an aqueous solution of the poly(L-phenylalanine) sodium sulfonate produced in Example 1 is added at least a stoichiometric quantity of zinc chloride. The resultant solution is dialyzed in a dialysis membrane tube having a molecular weight cutoff of about 1,000. Freeze drying the dialyzed polymer solution affords the poly(L-phenylalanine) zinc sulfonate as dry solids.

EXAMPLE 4

Poly(DL-phenylalanine) Sodium Sulfonate

Poly(DL-phenylalanine) sodium sulfonate is prepared by substituting poly(DL-phenylalanine) for poly(L-phenylalanine) in the procedure described in Example 1.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and the polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A—Mouthwash Solution

| | |
|---|---|
| Barrier Agent | 0.5–2.0% w/w |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B—Mouthwash Solution

| | |
|---|---|
| Plaque Barrier Agent | 0.5–3.0% w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C—Abrasive Dentrifice Gel

| | |
|---|---|
| Plaque Barrier Agent | 2.0–10.0% w/w |
| Fumed Silica (abrasive) | 55.0 |
| Sodium Lauryl Sulfate (detergent) | 1.5 |
| Glycerol (hymectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D—Chewing Gum

| | |
|---|---|
| Plaque Barrier Agent | 1.0–11.0% w/w |
| Gum Base | 21.3 |
| Sugar | 48.5–58.5 |
| Corn Syrup (Baume 45) | 18.2 |
| Flavors | 1.0 |
| | 100.0 |

EXAMPLE E—Nonabrasive Gel Dentrifrice

| | |
|---|---|
| Plaque Barrier Agent | 0.05–30.0% w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w | |
|---|---|---|
| Distilled Water | q.s. | |
| Sodium Saccharin (sweetener) | 0.20 | |
| Sodium Benzoate (preservative) | 0.30 | |
| FD&C Blue #1 (0.1%aq. soln.) | 0.27 | |
| D&C Yellow #10 (0.5% aq. soln.) | 0.50 | |
| Gelling agent | 18.00 | |
| Glycerol (Humectant) | 20.00 | |
| Cab-O-Sil M5 (Silicon Dioxide) | 1.00 | |
| Plaque Barrier Agent | 5.00 | (dry basis) |
| Flavor | 0.80 | |
| | 100.0 | |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

These compositions are preferably employed from one to three times daily in a routine oral hygiene program to prevent the attachment of plaque to the teeth.

Variations can, of course, be made without departing from the spirit or scope of the invention.

I claim:

1. A polyamino acid sulfonate having repeating units selected from the group consisting of the repeating units having structure (A),

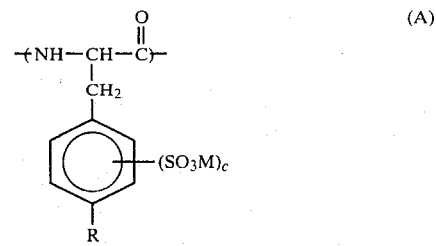

wherein R is selected from the group consisting of hydrogen and hydroxyl; subscript c, representing the average number of sulfonate groups per phenyl ring, has a value in the range of from about 0.5 to about 1.0; and M is an ion selected from the group consisting of lithium, sodium, potassium, calcium, magnesium zinc, aluminum, hydrogen and the ammonium salts derived from ammonia and the pharmaceutically acceptable organic amines.

2. An oral hygiene composition comprising an effective amount for preventing attachment of dental plaque to teeth of a polyamino acid sulfonate having repeating units selected from the group consisting of the repeating units having structure (A),

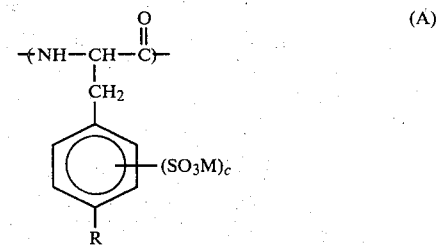

wherein R is selected from the group consisting of hydrogen and hydroxyl; subscript c, representing the average number of sulfonate groups per phenyl ring, has a value in the range of from about 0.5 to about 1.0; and M is an ion selected from the group consisting of lithium, sodium, potassium, calcium, magnesium, zinc, aluminum, hydrogen and the ammonium salts derived from ammonia and the pharmaceutically acceptable organic amines, in a pharmaceutically acceptable oral hygiene vehicle compatible with said polymer.

3. The composition of claim 2 wherein M is a metal selected from the group consisting of potassium, lithium, sodium, calcium, magnesium, zinc and aluminum.

4. A method of preventing attachment of dental plaque to teeth comprising periodically applying to the teeth a composition of claim 3.

5. The method of claim 4 wherein said composition is applied from about 1 to about 3 times per day.

* * * * *